United States Patent
Yang et al.

(10) Patent No.: US 7,833,929 B2
(45) Date of Patent: Nov. 16, 2010

(54) PROCESS FOR THE MANUFACTURE OF METHYLMERCAPTAN

(75) Inventors: Yiquan Yang, Xiamen (CN); Qi Wang, Xiamen (CN); Renchun Lin, Xiamen (CN); Hongbin Zhang, Xiamen (CN); Youzhu Yuan, Xiamen (CN); Weiping Fang, Xiamen (CN); Quanxing Zheng, Xiamen (CN); Shenjun Dai, Xiamen (CN); Xingguo Yan, Xiamen (CN); Aiping Chen, Xiamen (CN); Jan-Olaf Barth, Frankfurt am Main (DE); Christoph Weckbecker, Gründau-Lieblos (DE); Klaus Huthmacher, Gelnhausen (DE); Hubert Redlingshöfer, Münchsteinach (DE); Sabine Ackermann, Hanau (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 12/509,120

(22) Filed: Jul. 24, 2009

(65) Prior Publication Data
US 2010/0041548 A1 Feb. 18, 2010

Related U.S. Application Data

(62) Division of application No. 10/595,333, filed on Jan. 26, 2007, now Pat. No. 7,569,731.

(51) Int. Cl.
*B01J 23/00* (2006.01)
*B01J 21/00* (2006.01)
*B01J 20/00* (2006.01)
*B01J 29/00* (2006.01)
*B01J 37/00* (2006.01)

(52) U.S. Cl. .......... 502/300; 502/240; 502/255; 502/302; 502/303; 502/304; 502/305; 502/308; 502/309; 502/317; 502/321; 502/322; 502/323; 502/332; 502/349; 502/350; 502/355; 502/415; 502/439

(58) Field of Classification Search ........... 502/240, 502/255, 300, 302, 303, 304, 305, 308, 309, 502/317, 321, 322, 323, 332, 349, 350, 355, 502/415, 439
See application file for complete search history.

(56) References Cited

U.S. PATENT DOCUMENTS 3,928,444 A * 12/1975 Kamada et al. .......... 564/125

(Continued)

FOREIGN PATENT DOCUMENTS

CN 1207957 2/1999

(Continued)

OTHER PUBLICATIONS

Yang et al. Catalysis Letters (2201), 74(3-4), 221-225.

(Continued)

*Primary Examiner*—Cam N Nguyen
(74) *Attorney, Agent, or Firm*—Smith, Gambrell & Russell, LLP

(57) ABSTRACT

The present invention refers to a continuous process for the manufacture of methyl mercaptan using Mo—O—K-based catalysts. It is further described that the total selectivity of methylmercaptan can be increased by at least 1% by lowering the total gas hourly space velocity. The invention further refers to a process for the preparation of a solid, preformed catalyst system.

4 Claims, 1 Drawing Sheet

U.S. PATENT DOCUMENTS

| | | | |
|---|---|---|---|
| 4,043,934 A * | 8/1977 | Shuler et al. | 502/1 |
| 4,092,239 A * | 5/1978 | Moser | 208/213 |
| 4,105,589 A * | 8/1978 | Moser | 502/302 |
| 4,112,032 A * | 9/1978 | Blaszyk et al. | 264/42 |
| 4,116,996 A * | 9/1978 | Huang | 518/717 |
| 4,313,017 A | 1/1982 | McGinnis | |
| 4,333,855 A | 6/1982 | Gardner et al. | |
| 4,357,149 A | 11/1982 | West | |
| 4,371,458 A | 2/1983 | Eastman | |
| 4,389,304 A | 6/1983 | Eastman | |
| 4,438,218 A * | 3/1984 | Boorman et al. | 502/220 |
| 4,518,488 A * | 5/1985 | Wennerberg | 208/216 R |
| 4,570,020 A | 2/1986 | Ratcliffe | |
| 4,656,153 A * | 4/1987 | Wennerberg | 502/182 |
| 4,665,242 A | 5/1987 | Boulinquiez et al. | |
| 4,668,825 A | 5/1987 | Ratcliffe | |
| 5,486,628 A * | 1/1996 | Kemp | 549/536 |
| 5,494,875 A * | 2/1996 | Usui et al. | 502/206 |
| 5,580,839 A * | 12/1996 | Huffman et al. | 502/338 |
| 5,739,075 A * | 4/1998 | Matusz | 502/302 |
| 5,753,582 A * | 5/1998 | Garcin et al. | 502/323 |
| 5,874,630 A * | 2/1999 | Cook et al. | 568/71 |
| 6,034,020 A * | 3/2000 | Drake et al. | 502/60 |
| 6,143,689 A * | 11/2000 | Moy et al. | 502/170 |
| 6,383,974 B1 * | 5/2002 | Ishida et al. | 502/305 |
| 6,432,224 B1 * | 8/2002 | Minevski et al. | 148/272 |
| 6,770,589 B2 * | 8/2004 | Moy et al. | 502/170 |
| 7,235,173 B2 * | 6/2007 | Diehl et al. | 208/216 R |

FOREIGN PATENT DOCUMENTS

| | | |
|---|---|---|
| CN | 1207958 | 2/1999 |
| CN | 1528516 | 9/2004 |
| DE | 196 54 515 C1 | 10/1998 |
| EP | 0 104 507 A1 | 4/1964 |
| EP | 0 167 354 A1 | 1/1986 |
| EP | 0 832 878 A2 | 4/1998 |
| GB | 2 016 468 A | 9/1979 |

OTHER PUBLICATIONS

Wang, Qi et al. "The study of the promotion of Co to the supported catalyst K2Mo04 for the syntheses of methanethiol from H2S-containing syngas," 2003, pp. 64-68—Chemical.

Yang, Yi-Quan et al., "Study of the supported K . . . catalyst for methanethiol synthesis by one step from high . . . " Catalysis Letters, 2001, pp. 221-225, vol. 74, No. 3-4.

* cited by examiner

PROCESS FOR THE MANUFACTURE OF METHYLMERCAPTAN

This application is a divisional of U.S. patent application Ser. No. 10/595,333, filed 26 Jan. 2007, which is now U.S. Pat. No. 7,569,731.

The present invention refers to a continuous process for the manufacture of methyl mercaptan using Mo—O—K-based catalysts. The invention further refers to a process for the preparation of a solid, preformed catalyst system.

BACKGROUND OF THE INVENTION

Methylmercaptan is a well known intermediate for the production of organic compounds, such as sulfur containing amino acids, pesticides and dyes. Industrially, methylmercaptan, also known as methanethiol, is produced mainly for the synthesis of methionine, a widely used feed supplement for poultry.

Methylmercaptan is commercially produced by the heterogeneously catalyzed gas phase reaction of methanol and hydrogen sulfide. For example, EP-B-0832878 and DE-C-19654515 disclose a methanethiol preparation method based on the reaction of hydrogen sulfide ($H_2S$) with methyl alcohol ($CH_3OH$). EP-A-167,354 discloses a synthesis pathway based on the reaction of hydrogen sulfide with carbon monoxide (CO), wherein titanium dioxide ($TiO_2$) was employed as carrier and nickel oxide (NiO) or molybdenum oxide ($MoO_3$) as active component.

Chinese Patent Applications CN 1207957 and CN 1207958 disclose a series of catalysts useful for the methanethiol synthesis from high $H_2S$-containing synthesis gas, wherein the active component (Mo—S—K-based species) comes from the precursor of $K_2MoS_4$ or $(NH_4)_2MoS_4$ plus a potassium salt. In these Chinese patent applications, dimethylformamide [$(CH_3)_2NCOH$] and not water is chosen as solvent to dissolve the active component. The described process is hard to handle and expensive. Another disadvantage of the described catalyst and process seems to be the space-time-yield of methanethiol (0.08~0.19 $g \cdot h^{-1} \cdot ml^{-1}$ cat) which is rather low for a commercial catalyst.

EP-A-104507 describes a continuous process for reacting carbon oxides, sulfur or hydrogen sulfide, and hydrogen at elevated pressure and temperature. The reaction is carried out over a preformed, single-phase, solid catalyst system comprising a porous alumina containing support, on which a mixture of a manganese sulfide and a iron, nickel, zinc, chromium, cobalt, molybdenum or alkali metal sulfide is deposited. The described process is a continuous, vapor-phase reaction in the presence of a specified sulfur-containing or sulfide catalyst system containing manganese to produce methylmercaptan with improved conversions and yields. It is stated that by using the described catalyst system, the methane formation is kept to a minimum, which should result in an improved economic process. Formation of inert by-products, such as methane, should be avoided because these inert materials are difficult to separate from the recycle gases. It would build up in the recycle gas streams and would have to be vented periodically.

Other by-products of the synthesis of methylmercaptan from carbon oxides, sulfur or hydrogen sulfide and hydrogen include carbonyl sulfide, dimethyl sulfide, carbon bisulfide and dimethyl sulfide. Especially carbonyl sulfide formation should be kept to a minimum since carbonyl sulfide is an intermediate in the formation of methyl mercaptan. Low selectivities of carbonyl sulfide result in higher selectivities of methylmercaptan thus improving the overall yield of methylmercaptan and the whole economy of the process. Generally speaking, upon using carbon monoxide as carbon source, $CO_2$ is always formed as a product of the reaction in view of the water released in and carbon monoxide fed to the process. Carbon dioxide formation can be controlled by recycling the unreacted gases and by minimizing the concentration of water in the process.

U.S. Pat. No. 4,665,242 describes a process for the production of methylmercaptan by heating a gas comprising carbon monoxide and/or carbon dioxide, hydrogen sulfide and hydrogen in the presence of a catalyst based on a tungsten sulfide on an activated alumina substrate. In the process, unreacted gas is recycled to the feed gas stream, wherein the water which is formed during the reaction with the catalyst, is removed from the unreacted gas. The desiccation is carried out by passing the gas through a molecular sieve.

Although innumerous attempts have been started to improve the selectivity and yield of methylmercaptan preparation process, there is still a need for further improvements.

OBJECT OF THE INVENTION

It is an object of the present invention to provide a process for the manufacture of methylmercaptan with improved selectivity and yield.

SUMMARY OF THE INVENTION

The present invention is a continuous process for the manufacture of methylmercaptan by contacting an intimate mixture of carbon oxide, sulfur or hydrogen sulfide and hydrogen at elevated temperatures and pressures and a preformed, solid catalyst comprising an active component of Mo—O—K-based species, an active promoter and, optionally, a carrier and, optionally, recycling the unreacted gas to the feed gas stream in the process.

Surprisingly, it has been found, that in the present process, by decreasing the total gas hourly space velocity by 50%, preferably by 75%, the total selectivity of methylmercaptan is increased by at least 1%, depending on the reaction conditions chosen. It also has been found, that by using the present catalysts, the total selectivity of methylmercaptan is increased by at least 10% by increasing the reaction temperature from 220 up to 500° C.

Furthermore, with the above mentioned catalysts, the formation of the main by-products methane ($CH_4$), dimethylsulfide (DMS) and carbon bisulfide ($CS_2$) is kept to an absolute minimum (S<1%) under the reaction conditions of the process described in here. This effect presents a significant advantage for the technical realization of the process, since the formation of inert gases such as methane, which have to be vented periodically, is kept to an absolute minimum. Moreover, the separation and purification of the reaction product methylmercaptan (MC) is optimized, since only minor amounts of by-product such as carbon bisulfide, dimethylsulfide and methane are formed in the process.

Another objective of this invention is a process for preparing the solid, preformed catalyst system of the present invention.

BRIEF DESCRIPTION OF DRAWING

The invention will be further understood with reference to the accompanying drawing, which is a graph showing selectivity for methylmercaptan formation as a function of the total gas hourly space velocity and reaction temperature.

DETAILED DESCRIPTION OF THE INVENTION

Figure 1:
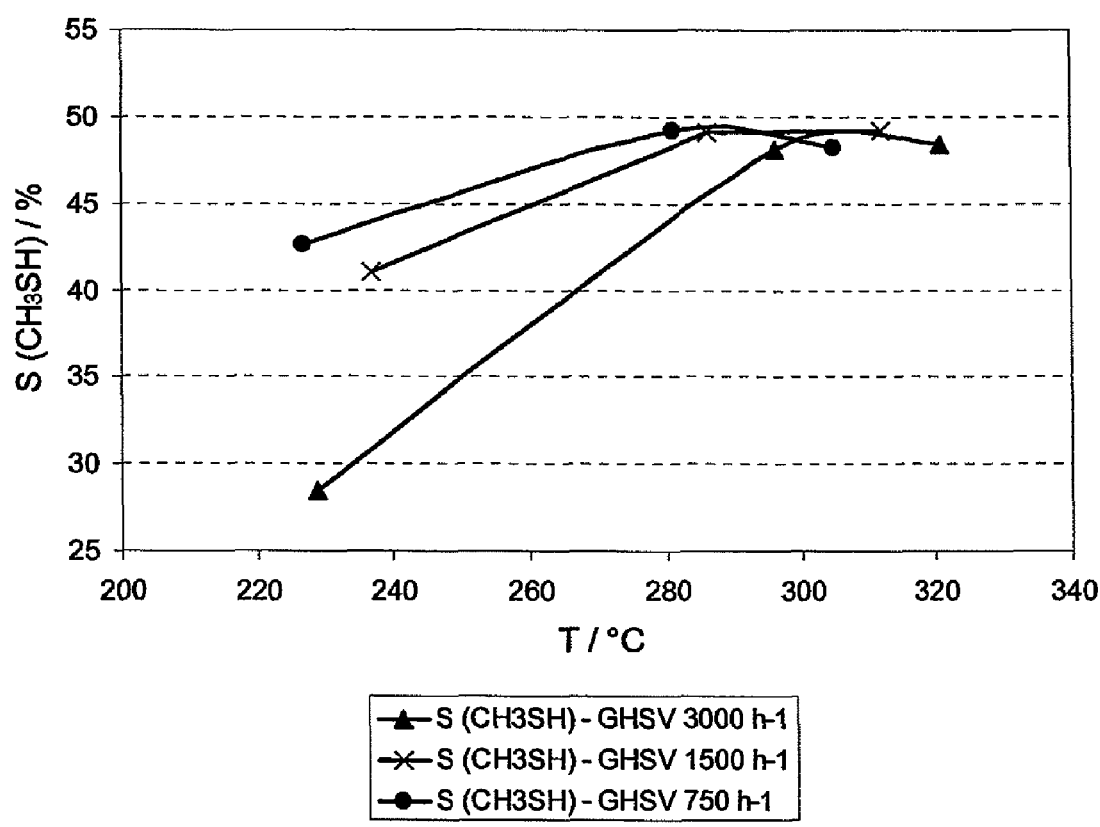

The present invention is a continuous process for the manufacture of methylmercaptan comprising contacting an intimate mixture of carbon oxides, such as carbon monoxide (CO) and/or carbon dioxide ($CO_2$), sulfur or hydrogen sulfide, and hydrogen at elevated temperature and pressure over a solid, preformed catalyst system comprising an active component and a carrier, and recycling the unreacted gaseous fraction to the feed gas stream in the process. The improvement of the present process consists of the fact that the gas to be recycled is separated from all by-products which are liquid at ambient temperature and pressure, and wherein the recycle gas is catalytically converted so as to only consist of carbon oxides, hydrogen and hydrogen sulfide. Furthermore, the reaction conditions of the process are adjusted to an optimum by increasing the reaction temperature and/or simultaneously decreasing the total gas hourly space velocity, thus resulting in an increased total selectivity of methylmercaptan formation. Finally, with the use of the catalysts described below, the formation of the by-products methane, dimethylsulfide and carbon bisulfide is kept to an absolute minimum (S<1%) under the relevant reaction conditions of the process.

The preformed solid catalyst of the present invention comprises an active component of Mo—O—K-based species, an active promoter and a carrier. Said active component of Mo—O—K-based species is preferably a precursor of molybdenum oxides, such as, for example, potassium molybdate ($K_2MoO_4$) or ammonium heptamolybdate [$(NH_4)_6Mo_7O_{24}$] plus a potassium salt or $MoO_3$ plus a potassium salt. The potassium salt useful in the present invention is selected from the group consisting of potassium acetate (KAc), potassium oxalate ($K_2C_2O_4$), potassium hydroxide (KOH) potassium carbonate ($K_2CO_3$), potassium nitrate ($KNO_3$), and potassium bicarbonate ($KHCO_3$). The potassium salt is then brought into an aqueous solution and is impregnated or coated in calculated amounts onto the support material prior to or after the deposition of the remaining active components by impregnation or coating techniques known to those skilled in the art. Examples of useful amounts of potassium salt useful for the purposes of the present invention are 1 to 50 wt. % $K_2O$, preferably 10 to 30 wt. % $K_2O$ of the total catalyst mass.

The active component of the present catalyst is impregnated or coated onto a carrier by various methods known to those skilled in the art, such as multi-step impregnation applied to the surface of the carrier or coating of the carrier with the active component. The active catalyst mass may also be pressed, extruded or pelletized to produce catalysts with various three dimensional forms and dimensions.

Active promoters useful in the present invention are represented by the general Formula $M_xO_y$, wherein M is selected from the group consisting of transition metal oxides and rare-earth metal oxides. Particularly suitable promoters are oxides of the group consisting of iron (Fe), molybdenum (Mo), manganese (Mn), cobalt (Co), nickel (Ni), lanthanum (La) and cerium (Ce), and x and y are integers from 1 to 5. Carriers useful in the present invention are selected from the group consisting of silicon dioxide ($SiO_2$), aluminum oxide ($Al_2O_3$), mixed silicon aluminum oxides, titanium dioxide ($TiO_2$), zeolites, clays or activated carbon.

When the active component is expressed by the amount of $K_2MoO_4$, the weight ratio of $K_2MoO_4/M_xO_y$/carrier equals to (0.01–0.80)/(0.01–0.1)/1, preferably (0.10–0.60)/(0.01–0.06)/1. However, when the active component is expressed by the amount of $MoO_3$ and $K_2O$, the weight ratio of $MoO_3/K_2O/M_xO_y$/carrier equals to (0.10–0.50)/(0.10–0.30)/(0.01–0.10)/1, preferably (0.10–0.30)/(0.10–0.25)/(0.01–0.06)/1, respectively.

Advantageously, the support useful in the present invention is selected from the group consisting of silicon dioxide (silica; $SiO_2$). The catalytic activity of the catalyst can be improved by using support materials with surface areas higher than 25 $m^2/g$. Advantageously, silica supports with surface areas of at least 60 $m^2/g$ are used as catalyst carriers. For practical technical purposes the high surface silica carriers are extruded or pelletized before or after the impregnation process. Preferably, Degussa Aerolyst™ carriers or similar high-surface area silica sources are used as supports.

The format of the support is not critical to the performance of the catalyst of the present invention and can have the form of three dimensional spheres, cylinders, rings, stars, pellets or other three dimensional forms or be in powder form which can be pressed, extruded or pelletized into three dimensional shapes. Advantageously the catalyst particles have a uniform particle size distribution (standard mean deviation: 5%, characterized by particle diameters of 0.2 mm to 20.0 mm.

The present invention further relates to a process for preparing a solid, preformed catalyst system comprising the steps of I) preparing an impregnation liquid of an aqueous solution of a salt of a transition metal or rare-earth metal and a precursor of $K_2MoO_4$ or $(NH_4)_6Mo_7O_{24}$ plus a potassium salt or $MoO_3$ plus a potassium salt; and II) impregnating a suitable carrier with such impregnation liquid, followed by drying the intermediate produced, and calcinating such intermediate to obtain the catalyst.

Alternatively, the present process for preparing a solid, preformed catalyst system can be carried out as a multi-step impregnation comprising the steps of A) preparing an impregnation liquid of an aqueous solution of a salt of a transition metal or rare-earth metal;

B) impregnating a suitable carrier with such impregnation liquid, followed by drying the intermediate produced, optionally calcinating such intermediate;

C) preparing an aqueous steeping solution of a precursor of $K_2MoO_4$ or $(NH_4)_6Mo_7O_{24}$ plus a potassium salt or $MoO_3$ plus a potassium salt; and D) steeping the intermediate produced in (B) with the aqueous steeping solution produced in (C) and then drying and calcinating the resultant catalyst.

An example for a preparation of a catalyst according to the present invention can be as follows:

1. A given quantity of a salt, such as nitrate, acetate or similar, of a transition metal or rare-earth metal is dissolved in a given quantity of distilled water to make an aqueous solution, with which a given quantity of the carrier chosen is impregnated for 3 to 5 hours, followed by drying at 50-130° C. for 1-3 hours to produce an intermediate. Subsequently, the resulting solid material is calcined at 300-600° C. for 5-6 h.

2. A given quantity of said precursor $K_2MoO_4$ or $(NH_4)_6Mo_7O_{24}$ plus a potassium salt or $MoO_3$ plus a potassium salt is dissolved in a given quantity of distilled water, with which the intermediate prepared in step (1) is impregnated for 7-9 hours, followed by drying at 50-130° C. for 2-4 hours, and calcination at 400-500° C. for 2-4 hours.

The multi-step impregnation is employed when ammonium heptamolybdate $(NH_4)_6Mo_7O_{24}$ or potassium molybdate $K_2MoO_4$ plus a potassium salt is used as the precursor of said active component, i.e., a given quantity of potassium salt chosen is dissolved in a given quantity of distilled water to form an aqueous solution, with which the intermediate modified with metal oxide prepared in step (1) is impregnated for 1-3 hours, followed by drying at 50-130° C. for 2-4 hours to produce an intermediate modified with both metal oxide and potassium salt. The next step is to impregnate the intermediate modified with both metal oxide and potassium salt prepared in the preceding steps with a given quantity of the aqueous solution of ammonium heptamolybdate $(NH_4)_6Mo_7O_{24}$ or potassium molybdate $K_2MoO_4$ for 7-9 hours, followed by drying at 50-130° C. for 2-4 hours, and calcination at 400-500° C. for 2-4 hours.

Optionally, in order to enhance the formation of the catalytic active species, the impregnation liquid and/or the steeping solution can be treated with alkyl amides, such as dimethylformamide and dimethyl acetamide, or an organic acid containing at least one carbon atom and at least one acid function. Particularly useful in the catalyst preparation process are organic acids, such as formic acid, acetic acid, propionic acid, butyric acid, pentanoic acid, hexanoic acid, acrylic acid, propionic acid, vinylacetic acid, methacrylic acid, crotonic acid, 4-pentenoic acid, sorbonic acid, oxalic acid, malonic acid, succinic acid, maleic acid, 3-hydroxybutyric acid, glutaric acid, adipic acid, citric acid, tartaric acid or ethylene diamine-tetracetic acid with citric acid being especially preferred.

Certain terms used herein have the following meaning with regard to the disclosure:

The term "active catalyst mass" means a composition of a catalyst support (carrier) impregnated or coated with various mixed oxides representing the catalytically active species.

The terms "support" and "carrier" are used simultaneously with the same meaning. The terms denote porous materials which have various three dimensional forms and dimensions and which provide a high specific surface area.

The term "single-phase" solid catalyst means a catalytically active mass of intimately mixed components which are solid materials.

The term "promoter" means the alkali or transition metal oxide or hydroxide or alkali or transition metal sulfide or hydrosulfide or any other alkali or transition metal salt precursor prior to or after sulfiding.

The term "sulfide" as used herein means a material including simple sulfides and hydrosulfides and complex sulfides.

The term "sulfiding" or "sulfided" as used herein relates to the treatment of the active catalyst mass with hydrogen sulfide or vaporous or liquid elemental sulfur and hydrogen under elevated temperature for a time such that the active catalyst mass is at least partially converted to the sulfide. Conversion of the catalyst from the oxide, hydroxide or any other salt to the sulfide state will change the weight of the compound somehow. Nevertheless, it will permit, prior to sulfiding, the use of the sulfide precursor within the same weight range as described herein for the sulfide in order to provide a catalyst system as defined for this invention.

The term "carbon oxides" as used herein relates to carbon monoxide or carbon dioxide or combinations thereof.

The term "(gas hourly) space velocity" as used herein, refers to the total volume (usually in liters) of carbon oxides, hydrogen and hydrogen sulfide passing through a unit volume (usually 1 liter) of the catalyst system during one hour measured at a standard temperature and pressure.

The term "yield" denotes the number of moles of CO or $CO_2$ per initial 100 moles actually converted into methylmercaptan or any other specified by-product.

As used herein, the term "conversion" indicates the percentage of the moles of carbon monoxide that were converted to methylmercaptan or any other reaction product, The part percentage which gives rise to methylmercaptan alone is called selectivity.

Thus, Yield=Conversion×Selectivity

Carbon monoxide, hydrogen sulfide or elemental sulfur and hydrogen are the preferred starting materials for the process of the present invention. Carbon dioxide may be used to replace part or all of the carbon monoxide, but carbon monoxide is more reactive and provides higher conversions than carbon dioxide at high space velocities and lower pressures.

Mixtures of carbon monoxide and hydrogen in various stoichiometric ratios are also known as synthesis gas and are easily produced by various methods, such as partial oxidation of hydrocarbons, steam reforming of natural gas, naphtha and high vacuum residues from crude oil distillation or coal gasification. The well known process of steam reforming of natural gas (methane) can be exemplified according to the equation:

$$CH_4+H_2O \rightarrow CO+3H_2 \qquad (Equ. 1)$$

Hydrogen sulfide may be supplied to the process or it may be formed in situ in the process by reacting elemental sulfur in the molten or vapor state either before, during or after contacting them with the feed of reactants in the reactor. Elemental sulfur may be fed together with carbon oxides and hydrogen directly to the reactor, since under the temperature and pressure conditions of the present invention, sulfur will be in the molten state and will form $H_2S$ immediately upon contact with hydrogen. The chemical reactions can be exemplified as:

$$CO+H_2S+2H_2 \rightarrow CH_3SH+H_2O \qquad (Equ. 2)$$

$$CO_2+H_2S+3H_2 \rightarrow CH_3SH+2H_2O \qquad (Equ. 3)$$

$$CO+S+3H_2 \rightarrow CH_3SH+H_2O \qquad (Equ. 4)$$

$$CO_2+S+4H_2 \rightarrow CH_3SH+2H_2O \qquad (Equ. 5)$$

It is believed that, over the catalysts described herein, the reaction procedes via the hydrogenation of the intermediate carbonyl sulfide (COS) which is formed upon the reaction of carbon monoxide and hydrogen sulfide:

$$CO+H_2S \rightarrow COS+H_2 \qquad (Equ. 6)$$

$$COS+3H_2 \rightarrow CH_3SH+H_2O \qquad (Equ. 7)$$

For the process described herein, it has been found, that, by using the present catalysts, the yield of the intermediate carbonyl sulfide can be minimized by decreasing the total gas hourly space velocity and/or by increasing the reaction temperature, thus resulting in increased yields of methylmercaptan. Furthermore, by using the catalysts described herein, it has been found that the formation of methanol and dimethylether as reaction products of carbon oxides with hydrogen does not occur within the temperature and pressure range described herein. Consequently, using carbon monoxide as carbon source, only carbon dioxide, methane, carbonyl sulfide, carbon bisulfide, and dimethylsulfide are the only potential reaction by-products.

The feed rate of the reactants through the catalyst bed of the reactor is reported herein as total gas hourly space velocity. The process of the present invention can be operated at space velocities in the range of 1 to 10000 $h^{-1}$, preferably of from 100 to 5000 $h^{-1}$, preferably of from 300 to 5000 $h^{-1}$, and more preferably from 750 to 3000 $h^{-1}$. The optimum space velocity employed will vary between 100 and 5000 $h^{-1}$ depending upon the other conditions of the process, such as temperature, pressure and molar ratio of the reactants. It has been found, that the lower the space velocity the higher the selectivity for methylmercaptan and the lower the formation of undesired by-products, such as carbonyl sulfide.

The molar ratio of reactants in the feed mixture, i.e., carbon oxide, hydrogen sulfide or elemental sulfur and hydrogen should be chosen so as to result in an excess of hydrogen sulfide. Preferably, the molar ratios of $CO_{1-2}/H_2S/H_2$ ranges between 1/1/0 and 1/10/10, preferably between 1/2/1 and 1/4/4. When utilizing elemental sulfur to replace $H_2S$ in the feed, the molar ratio of the reactants $CO_{1-2}/S/H_2S/H_2$ will preferably range between 1/1/1/1 and 1/10/10/10, more preferably between 1/2/2/1 and 1/4/4/4. As shown in the equation below, the presence of hydrogen is not a prerequisite for the formation of methylmercaptan. With the process and catalysts of the present invention, methylmercaptan can be readily formed by using $H_2S$ as sulfur source in the absence of hydrogen.

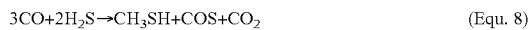

$$3CO+2H_2S \rightarrow CH_3SH+COS+CO_2 \quad \text{(Equ. 8)}$$

It is advantageous to carry out the present process using a series of fixed catalyst beds or a reactor comprising one or multiple (n=1-10) reaction zones for the chemical reaction, in which one or more of the reacting gases can be fed between the reaction zones. The catalyst may be arranged in fixed beds with intermediate gas injection or multitubular reactors for a better temperature control.

According to a preferred embodiment of the process of this invention, the reactants carbon oxide, sulfur, hydrogen sulfide and hydrogen are mixed in the desired molar ratio before being fed to the reactor. The reactants may be introduced separately at different zones/catalysts beds which are sequentially arranged in the reactor to increase the overall yield of methylmercaptan. Preferably hydrogen and/or hydrogen sulfide are introduced between the catalyst beds, thus increasing the overall yield of methylmercaptan.

The reactants are advantageously preheated to at least 120° C. prior to entering the reactor. The preferred preheating temperature ranges from 150 to 350° C. Using elemental sulfur as sulfur source, the reacting gases may be either fed through liquid sulfur at temperatures preferably between 150 and 450° C. or they may be mixed with gaseous sulfur prior to entering the reactor.

The temperature in the reactor is generally controlled by the temperature of the catalyst bed which ranges from at least 200° C. to up to 500° C., preferably between at least 250° C. and 500° C., preferably between 250 and 400° C., more preferably between 220 and 320° C. When sulfur is used as reactant in the process, the temperature and pressure in the reactor should be at least sufficient to maintain sulfur in the liquid state. Although the reaction is exothermic, further heat is supplied externally.

It has been found that, in the present process, the formation of the by-product carbonyl sulfide can be minimized by gradually increasing the reaction temperature. This effect is interesting since usually the formation of by-products is supported by increasing the reaction temperature. The pressure in the reactor is generally above 2 bar, preferably ≧4. To increase the yield of methylmercaptan the pressure is preferably within the range of 4-60 bar, more preferably in the range of 5-40 bar.

Prior to starting the reaction, the catalysts are preconditioned in a flow of hydrogen or carbon monoxide or carbon monoxide and hydrogen at temperatures between 20 and 500° C., preferably between 200 and 400° C., and pressures between 1 and 10 bar. Subsequently, the catalysts are exposed to a flow of hydrogen sulfide or hydrogen and elemental sulfur under reaction conditions. The total time for the preconditioning process may range from 6 hours (h) to 48 hours, preferably of from 10 to 24 h.

An improvement in methylmercaptan yield and higher selectivities of this product is achieved when the catalyst is preconditioned in a stream of hydrogen or carbon monoxide and hydrogen or carbon monoxide prior to sulfurization of the catalyst by exposing the catalyst to hydrogen sulfide or a stream of hydrogen and sulfur which precedes the catalytic reaction.

The process is further characterized by recycling the unconsumed reactants to the feed gas stream in the process after a first pass through the reactor. Preferably, all reaction products liquid at 0-5° C. and at ambient pressure should be separated from the gaseous products. This may be achieved by quenching the gases leaving the reaction zone and separating all liquids such as methylmercaptan, dimethyl sulfide, water and carbon bisulfide. An essential characteristic of this process is that the gas being recycled is completely water free to avoid an accumulation of water in the process, which would have a negative impact on the yield of methylmercaptan and the process selectivity.

The present invention is explained in more detail in the following with the aid of embodiment examples.

EXAMPLE 1

Preparation of the Catalysts A Through E

Catalyst A

An aqueous solution of 62.0 g of $K_2MoO_4$ dissolved in 130 ml of distilled water is prepared, to which 24.9 g of cobalt nitrate and 60 ml of ammonium hydroxide are added successively under continuous agitation. After complete dissolution of the cobalt nitrate, 40 g of citric acid are added under stirring to generate the impregnation liquid. 150 g of $SiO_2$ are brought into contact for 24 h with the impregnation liquid prepared above. Thereafter, the wet catalyst is filtered and dried at room temperature and then dried in an oven at 80° C. for 2 h, followed by calcination at 500° C.

Catalyst B

1. An aqueous solution of 8.4 g of ferric nitrate and 13.0 g of nickel nitrate dissolved in 120 ml of distilled water is prepared, to which 10 g of critic acid are then added, under continuous agitation for 30 min to generate the impregnation liquid. Subsequently, 100 g of $SiO_2$ are soaked in the impregnation liquid prepared above for 24 h, followed by filtration, drying of the wet catalyst cake at room temperature, followed by drying at 80° C. in an oven for 2 h, and calcination at 500° C. An $Fe_2O_3$—NiO-supported carrier was obtained.
2. An Aqueous Solution of 41.4 g of Potassium Molybdate dissolved in 110 ml of distilled water is prepared, to which 10 ml of ammonium hydroxide are added under stirring, followed by adding 10 g of citric acid to adjust the pH of the solution. The stirring is maintained until the citric acid is completely dissolved to produce a steeping solution. Finally, the $Fe_2O_3$—NiO-supported carrier produced above is impregnated in the steeping solution for 24 h, followed by filtration, drying at room temperature, and by drying at 80° C. in an oven for 2 h, followed by calcination at 500° C.

Catalyst C

An aqueous solution 33.0 g of potassium carbonate and 46 g of ammonium molybdate dissolved in 130 ml of distilled water is prepared, to which 10 ml of ammonium hydroxide are added under stirring, followed by adding, under stirring, 24.9 g of cobalt nitrate and 35 ml of ammonium hydroxide to the aqueous solution prepared above. After dissolution of all added ingredients, 50 g of citric acid are added to adjust the pH of the solution, while maintaining stirring for 30 min to produce an impregnation liquid with pH 7.3. Finally, 150 g of $SiO_2$ (20-30 mesh) are impregnated in the impregnation liquid for 24 h, then filtered, dried at room temperature, followed by drying at 80° C. in an oven for 2 h, and calcination at 500° C.

Catalyst D 1. 7.3 ml of an aqueous solution of cerium nitrate (concentration of 0.1032 g/ml) is mixed with 170 ml of distilled water to lower the concentration of cerium nitrate. 150 g of $SiO_2$ (20-30 mesh) is impregnated for 24 h into the impregnation liquid prepared above, then filtered, dried at room temperature, followed by drying in an oven at 80° C. for 2 h, and calcination at 500° C. An $CeO_2$-supported carrier was obtained.
2. An aqueous solution of 62.0 g of potassium molybdate dissolved in 130 ml of distilled water is prepared, to which 10 ml of ammonium hydroxide are added under stirring. After dissolution of all ingredients, 24.9 g of cobalt nitrate, 30 ml of ammonium hydroxide and 40 g of citric acid are added to the aqueous solution prepared above to adjust the pH of the aqueous solution, while maintaining the agitation for 30 min to produce a steeping solution with pH 8.6. Finally, the $CeO_2$-supported carrier prepared above is impregnated in the steeping solution for 24 h, then filtered, dried at room temperature, followed by drying in an oven at 80° C. for 2 h, and calcination at 500° C.

Catalyst E

1. Under stirring, 22.9 g of nickel nitrate, together with 15 ml of ammonium hydroxide and 10 g of citric acid are dissolved in 165 ml of distilled water, while maintaining the agitation for 30 min to produce an impregnation liquid with pH 7.1, in which 150 g of $SiO_2$ (20~30 mesh) are impregnated for 24 h, then filtered, dried at room temperature, followed by drying in an oven at 80° C. for 2 h, and calcination at 500° C. to generate a NiO-supported carrier.
2. 62.0 g of potassium molybdate are dissolved in 160 ml of distilled water to form an aqueous solution, to which 15 ml of ammonium hydroxide, together with 15 g of citric acid are added under stirring, keeping agitating for 30 min to generate a steeping solution with pH 8.1. Finally, the NiO-supported carrier prepared above is impregnated in the steeping solution for 24 h, then filtered, dried at room temperature, followed by drying in an oven at 80° C. for 2 h, and calcination at 500° C.

EXAMPLE 2

The catalysts A-E described in Example 1 were tested under the following reaction conditions: the total gas hourly space velocity was 3000 $h^{-1}$, the reactant molar ratio for $CO/H_2/H_2S$ was 1/2/1, respectively and the catalyst bed temperature was 300° C. (maximum) and the absolute pressure was 7 bar. The catalytic activity was evaluated for a single-pass of the reactor. Determination of conversions and yields were made as described above.

TABLE 1

| Catalyst | Conversion (CO)/% | Yield (MC)/% | Yield (MC)/ $g_{MC}g_{cat}^{-1}h^{-1}$ |
|---|---|---|---|
| Catalyst A | 28 | 10 | 0.20 |
| Catalyst B | 28 | 11 | 0.24 |
| Catalyst C | 29 | 12 | 0.25 |
| Catalyst D | 27 | 12 | 0.24 |
| Catalyst E | 24 | 10 | 0.25 |

CO = carbon monoxide
MC = methylmercaptan

EXAMPLE 3

Table 2 shows a comparison of the catalytic activity of a catalyst consisting of $Co_2O_3$—$K_2MoO_4$ impregnated on a $SiO_2$ carrier as compared to a reference catalyst of pure $K_2MoO_4$ supported on the same carrier material. The materials were tested under the following reaction conditions: the total gas hourly space velocity was 3000 $h^{-1}$, the reactant molar ratio for $CO/H_2/H_2S$ was 2/7/1, respectively, the catalyst bed temperature was 350° C. and the absolute pressure was 10 bar. The catalytic activity was evaluated for a single-pass of the reactor. Determination of conversions and yields were made as described above.

TABLE 2

| Catalyst | Conversion (CO)/% | Yield (MC)/% | Selectivity (MC)/% | Yield (MC)/ $g_{MC}g_{cat}^{-1}h^{-1}$ |
|---|---|---|---|---|
| $Co_2O_3/K_2MoO_4/SiO_2$ | 8 | 3 | 38 | 0.07 |
| $K_2MoO_4/SiO_2$ (reference material) | 2 | 0.5 | 25 | 0.01 |

EXAMPLE 4

The above mentioned catalysts A-E were tested under the following reaction conditions: the total gas hourly space velocity was 3000 $h^{-1}$, the reactant molar ratio for $CO/H_2/H_2S$ was 1/1/2. Another test was performed in the absence of hydrogen ($CO/H_2S=1/3$), respectively. For both cases, the catalyst bed temperature was 320° C. (maximum) and the absolute pressure was 7 bar. The catalytic activity was evaluated for a single-pass of the reactor. Determination of conversions and yields were made as described above. Example 4 clearly demonstrates the high space time yields of methylmercaptan produced in the present process.

TABLE 3

| | $CO/H_2/H_2S = 1/1/2$ | | | $CO/H_2S = 1/3$ | | |
|---|---|---|---|---|---|---|
| Catalyst | Conversion (CO)/% | Yield (MC)/% | Yield (MC)/ $g_{MC}g_{cat}^{-1}h^{-1}$ | Conversion (CO)/% | Yield (MC)/% | Yield (MC)/ $g_{MC}g_{cat}^{-1}h^{-1}$ |
| Catalyst A | 71 | 32 | 0.59 | 93 | 24 | 0.47 |
| Catalyst B | 71 | 32 | 0.68 | 93 | 26 | 0.54 |

TABLE 3-continued

| | CO/H$_2$/H$_2$S = 1/1/2 | | | CO/H$_2$S = 1/3 | | |
|---|---|---|---|---|---|---|
| Catalyst | Conversion (CO)/% | Yield (MC)/% | Yield (MC)/ g$_{MC}$g$_{cat}^{-1}$h$^{-1}$ | Conversion (CO)/% | Yield (MC)/% | Yield (MC)/ g$_{MC}$g$_{cat}^{-1}$h$^{-1}$ |
| Catalyst C | 72 | 33 | 0.68 | 91 | 24 | 0.48 |
| Catalyst D | 70 | 32 | 0.66 | 94 | 25 | 0.51 |
| Catalyst E | 72 | 32 | 0.77 | 92 | 25 | 0.60 |

EXAMPLE 5

Catalyst B was tested under the following reaction conditions: the total gas hourly space velocity was 750 h$^{-1}$ 1500 h$^{-1}$, or 3000 h$^{-1}$, the reactant molar ratio for CO/H$_2$/H$_2$S was 1/1/2, the catalyst bed temperature was varied between 220° C. (minimum) and 320° C. (maximum) and the absolute pressure was 7 bar. The catalytic activity was evaluated for a single-pass of the reactor. FIG. 1 shows the selectivity for methylmercaptan formation as a function of the total gas hourly space velocity and the reaction temperature.

Table 4 demonstrates that the formation of the by-products methane, dimethylsulfide and carbon bisulfide is kept to an absolute minimum (S<1%) under the three reaction conditions of the process.

TABLE 4

| GHSV/ h$^{-1}$ | S (MC)/ % | S (CO$_2$)/ % | S (COS)/ % | S (CH$_4$)/ % | S (DMS)/ % | S (CS$_2$)/ % |
|---|---|---|---|---|---|---|
| 750 | 43 | 40 | 17 | 0 | <1 | <1 |
| 1500 | 41 | 39 | 20 | <1 | <1 | <1 |
| 3000 | 28 | 31 | 39 | 0 | 0 | <1 |

GHSV = gas hourly space velocity
S = selectivity

EXAMPLE 6

Catalyst D was tested under the following reaction conditions: the total gas hourly space velocity was 3000 h$^{-1}$, the reactant molar ratio for CO/H$_2$/H$_2$S was 1/1/2, the catalyst bed temperature was varied between 220° C. (minimum) and 320° C. (maximum) and the absolute pressure was 7 bar. Table 5 shows the selectivity for methylmercaptan, carbonyl sulfide, carbon dioxide, methane, dimethylsulfide and carbon bisulfide formation as a function of the temperature of the catalyst bed. It should be noted, that the formation of methane, dimethylsulfide and carbonyl bisulfide is kept to an absolute minimum (S<1%) under the various reaction conditions. The catalytic activity was evaluated for a single-pass of the reactor.

TABLE 5

| Temp. ° C. | S (MC)/ % | S (CO$_2$)/ % | S (COS)/ % | S (CH$_4$)/ % | S (DMS)/ % | S (CS$_2$)/ % |
|---|---|---|---|---|---|---|
| 238 | 29 | 31 | 40 | 0 | 0 | 0 |
| 311 | 48 | 43 | 8 | <1 | <1 | <1 |
| 333 | 49 | 43 | 6 | 1 | <1 | <1 |

S = selectivity
MC = methylmercaptan
CO$_2$ = carbon dioxide
COS = Carbonyl sulfide
CH$_4$ = methane
DMS = dimethylsulfide
CS$_2$ = carbon bisulfide

What is claimed is:

1. A process for preparing a solid, preformed catalyst system comprising the steps of:
    A) preparing an impregnation liquid of an aqueous solution of a salt of a transition metal or rare-earth metal;
    B) impregnating a carrier with said impregnation liquid, followed by drying the intermediate produced, optionally calcining said intermediate;
    C) preparing a solution of a precursor of K$_2$MoO$_4$ or (NH$_4$)$_6$Mo$_7$O$_{24}$ plus a potassium salt or MoO$_3$ plus a potassium salt; and
    D) steeping the intermediate produced in (B) with the solution produced in (C) and then drying and calcining the resultant catalyst.

2. The process according to claim 1, wherein the impregnation liquid and/or the solution is treated with alkyl amides, or an organic acid containing at least one carbon atom and at least one acid function.

3. The process according to claim 2, wherein the organic acid is citric acid.

4. The process according to claim 1, wherein the alkyl amide is dimethylformamide or dimethyl acetamide, and the organic acid is formic acid, acetic acid, propionic acid, butyric acid, pentanoic acid, hexanoic acid, acrylic acid, propionic acid, vinylacetic acid, methacrylic acid, crotonic acid, 4-pentenoic acid, sorbonic acid, oxalic acid, malonic acid, succinic acid, maleic acid, 3-hydroxybutyric acid, glutaric acid, adipic acid, citric acid, tartaric acid or ethylene diaminetetracetic acid.

* * * * *